(12) United States Patent
Pontillo et al.

(10) Patent No.: US 6,951,858 B2
(45) Date of Patent: *Oct. 4, 2005

(54) GONADOTROPIN-RELEASING HORMONE RECEPTOR ANTAGONISTS AND METHODS RELATING THERETO

(75) Inventors: Joseph Pontillo, San Diego, CA (US); Zhiqiang Guo, San Diego, CA (US); Dongpei Wu, San Diego, CA (US)

(73) Assignee: Neurocrine Biosciences, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/705,762

(22) Filed: Nov. 10, 2003

(65) Prior Publication Data

US 2005/0075339 A1 Apr. 7, 2005

Related U.S. Application Data

(63) Continuation of application No. 10/211,992, filed on Aug. 2, 2002, now Pat. No. 6,673,796.
(60) Provisional application No. 60/309,965, filed on Aug. 2, 2001, provisional application No. 60/309,911, filed on Aug. 2, 2001, and provisional application No. 60/309,981, filed on Aug. 2, 2001.

(51) Int. Cl.[7] .................... C07D 253/075; A61K 31/53; A61P 15/00; A61P 15/08; A61P 15/018
(52) U.S. Cl. ...................................... 514/242; 544/182
(58) Field of Search ........................... 544/182; 514/242

(56) References Cited

U.S. PATENT DOCUMENTS

| 5,780,437 A | 7/1998 | Goulet et al. ................. 514/19 |
| 5,849,764 A | 12/1998 | Goulet et al. ................ 514/337 |
| 6,673,796 B2 * | 1/2004 | Pontillo et al. ............. 514/242 |

FOREIGN PATENT DOCUMENTS

| EP | 748 800 | 12/1996 |
| JP | 48-28026 | 8/1971 |
| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | WO 99/33831 | 7/1999 |
| WO | WO 00/56739 | 9/2000 |
| WO | WO 00/69859 | 11/2000 |
| WO | WO 01/29044 | 4/2001 |

OTHER PUBLICATIONS

Al–Damluji et al., "$\alpha_{1B}$ Adrenergic Receptors in Gonadotrophin–Releasing Hormone Neurones:Relation to Transport–P," *British Journal of Pharmacology* 132:336–344, 2001.

Burch, "Nitrofuryl Heterocycles. X.[1] Analogs of 6–(5–Nitro–2–furyl)–as–Triazine–3,5(2H,4H)–dione," *Journal of Medicinal Chemistry* 13:288–291, 1970.

Cho et al., "Discovery of a Novel, Potent,a nd Orally Active Nonpeptide Antagonist of the Human Luteinizing Hormone–Releasing Hormone (LHRH) Receptor,"*J Med Chem* . 41(22):4190–4195, Oct. 22, 1998.

Huirne, J. et al., "Gonadotropin–Releasing–Hormone–Receptor Antagonists," *Lancet* 358(9295):1793–1803, Nov. 2001.

Stanislaus et al., "Regulation of G9/11$\alpha$ by the Gonadotropin–Releasing Hormone Receptor," *Molecular Endocrinology* 11:738–746, 1997.

\* cited by examiner

*Primary Examiner*—Venkataraman Balasubramanian
(74) *Attorney, Agent, or Firm*—Seed IP Law Group PLLC

(57) ABSTRACT

GnRH receptor antagonists are disclosed which have utility in the treatment of a variety of sex-hormone related conditions in both men and women. The compounds of this invention have the structure:

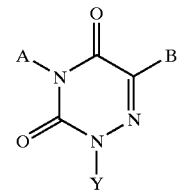

wherein $R_1$, $R_2$, $R_{3a}$, $R_{3b}$, $R_4$, $R_5$, and n are as defined herein, including stereoisomers, prodrugs and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

13 Claims, No Drawings

SEQUENCE LISTING

<160> NUMBER OF SEQ ID NOS: 2

<210> SEQ ID NO 1
<211> LENGTH: 10
<212> TYPE: PRT
<213> ORGANISM: Homo sapiens

<400> SEQUENCE: 1

Glu His Trp Ser Tyr Gly Leu Arg Pro Gly
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide GnRH agonist.
<220> FEATURE:
<221> NAME/KEY: MOD_RES
<222> LOCATION: 6
<223> OTHER INFORMATION: D-Leucine

<400> SEQUENCE: 2

Glu His Trp Ser Tyr Leu Leu Arg Pro
1               5

GONADOTROPIN-RELEASING HORMONE RECEPTOR ANTAGONISTS AND METHODS RELATING THERETO

CROSS-REFERENCES TO RELATED APPLICATIONS

This application is a continuation of U.S. application Ser. No. 10/211,992 filed Aug. 2, 2002 (now U.S. Pat. No. 6,673,796), which claims the benefit of U.S. Provisional Patent Application No. 60/309,965 filed Aug. 2, 2001; U.S. Provisional Patent Application No. 60/309,911 filed Aug. 2, 2001; and U.S. Provisional Patent Application No. 60/309,981, filed Aug. 2, 2001; which applications are incorporated herein by reference in their entireties.

STATEMENT REGARDING FEDERALLY SPONSORED RESEARCH OR DEVELOPMENT

Partial funding of the work described herein was provided by the U.S. Government under Grant No. R43-HD38625 provided by the National Institute of Health. The U.S. Government may have certain rights in this invention.

BACKGROUND OF THE INVENTION

1. Field of the Invention

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) (SEQ ID NO: 1) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine lelomyoma, and precocious puberty. For example, peptidic GnRH agonists, such as leuprorelin (pGlu-His-Trp-Ser-Tyr-D-Leu-Leu-Arg-Pro-NHEt) (SEQ ID NO: 2), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780,437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

BRIEF SUMMARY OF THE INVENTION

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

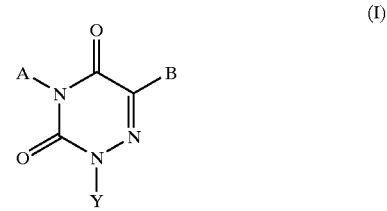

including stereoisomers, prodrugs and pharmaceutically acceptable salts thereof, wherein A, B and Y are as defined below.

The GnRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

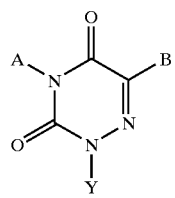

(I)

including stereoisomers, prodrugs and pharmaceutically acceptable salts thereof,
wherein:
A is —$(CR_{3a}R_{3b})_n NR_1R_2$ or $R_5$;
Y is —$(CR_{3a}R_{3b})_n NR_1R_2$, $R_4$, or $R_5$;
with the proviso that one of A or Y, but not both, is —$(CR_{3a}R_{3b})_n NR_1R_2$;
B is $R_4$ or —X—$R_5$;
X is O, S or a direct bond;
n is 2, 3 or 4;
$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —$C(R_8)(=NR_9)$ or —$C(NR_6R_7)(=NR_9)$;
or $R_1$ and $R_2$ taken together with the nitrogen atom to which they are attached form a heterocycle or a substituted heterocycle;
$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —$COOR_{10}$ or —$CONR_6R_7$;
or $R_{3a}$ and $R_{3b}$ taken together with the carbon atom to which they are attached form a homocycle, substituted homocycle, heterocycle or substituted heterocycle;

or $R_{3a}$ and the carbon to which it is attached taken together with $R_1$ and the nitrogen to which it is attached form a heterocycle or substituted heterocycle;
$R_4$ is arylalkyl, substituted arylalkyl, heteroarylalkyl or substituted heteroarylalkyl;
$R_5$ is aryl, substituted aryl, heteroaryl, or substituted heteroaryl;
$R_6$ and $R_7$ are the same or different independently hydrogen, alkyl, substituted alkyl, aryl, substituted aryl, arylalkyl, substituted arylalkyl, heterocycle, substituted heterocycle, heterocyclealkyl or substituted heterocyclealkyl;
$R_8$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;
$R_9$ is independently hydrogen, alkyl, substituted alkyl, aryl, substituted aryl, arylalkyl, substituted arylalkyl, heterocycle, substituted heterocycle, heterocyclealkyl or substituted heterocyclealkyl; and
$R_{10}$ is hydrogen, alkyl, or substituted alkyl.

As used herein, the above terms have the following meaning:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. The term "higher alkyl" has the same meaning as alkyl but contains from 2 to 10 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as a "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl- 1 -butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —$(CH_2)_2$phenyl, —$(CH_2)_3$phenyl, —$CH(phenyl)_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocyclic ring") means a 4- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

"Homocycle" (also referred to herein as "homocyclic ring") means a saturated or unsaturated (but not aromatic) carbocyclic ring containing from 3–7 carbon atoms, such as cyclopropane, cyclobutane, cyclopentane, cyclohexane, cycloheptane, cyclohexene, and the like.

The term "substituted" as used herein means any of the above groups (i.e., alkyl, aryl, arylalkyl, heteroaryl, heteroarylalkyl, homocycle, heterocycle and/or heterocyclealkyl) wherein at least one hydrogen atom is replaced with a substituent. In the case of an oxo substituent ("=O"), two hydrogen atoms are replaced. When substituted one or more of the above groups are substituted, "substituents" within the context of this invention include halogen, hydroxy, oxo, cyano, nitro, amino, alkylamino, dialkylamino, alkyl, alkoxy, alkylthio, haloalkyl, aryl, arylalkyl, heteroaryl, heteroarylalkyl, heterocycle and heterocyclealkyl, as well as —NR$_a$R$_b$, —NR$_a$C(=O)R$_b$, —NR$_a$C(=O)NR$_a$NR$_b$, —NR$_a$C(=O)OR$_b$—NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. In addition, the above substituents may be further substituted with one or more of the above substituents, such that the substituent substituted alky, substituted aryl, substituted arylalkyl, substituted heterocycle or substituted heterocyclealkyl. R$_a$ and R$_b$ in this context may be the same or different and independently hydrogen, alkyl, haloalkyl, substituted alkyl, aryl, substituted aryl, arylalkyl, substituted arylalkyl, heterocycle, substituted heterocycle, heterocyclealkyl or substituted heterocyclealkyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Alkylthio" means an alkyl moiety attached through a sulfur bridge (i.e., —S-alkyl) such as methylthio, ethylthio, and the like.

"Alkylsulfonyl" means an alkyl moiety attached through a sulfonyl bridge (i.e., —SO$_2$-alkyl) such as methylsulfonyl, ethylsulfonyl, and the like.

"Alkylamino" and "dialkylamino" mean one or two alkyl moiety attached through a nitrogen bridge (i.e., —N-alkyl) such as methylamino, ethylamino, dimethylamino, diethylamino, and the like.

Depending upon the selection of A, B and Y, representative compounds of the invention include the following structures (II) through (IV);

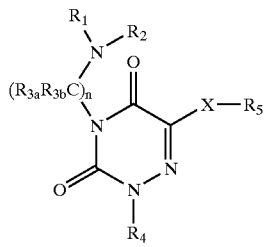

II

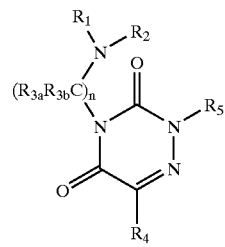

III

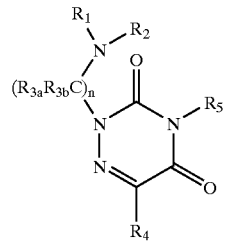

IV

With regard to the "R$_1$R$_2$N(CR$_{3a}$R$_{3b}$)$_n$—" moiety of structure (I), n may be 2, 3 or 4. Accordingly, this moiety may be represented by the following structure (i) when n is 2, (ii) when n is 3, and structure (iii) when n is 4:

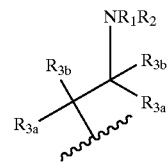

(i)

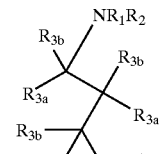

(ii)

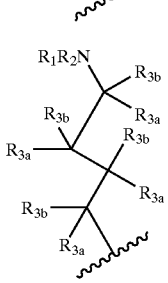

(iii)

wherein each occurrence of $R_{3a}$ and $R_{3b}$ above may be the same or different, and are as defined above. For example, when each occurrence of $R_{3a}$ and $R_{3b}$ in structures (i), (ii) and (iii) is hydrogen, the "$R_1R_2N(CR_{3a}R_{3b})_n$—" moiety has the structure $R_1R_2N(CH_2)_2$—, $R_1R_2N(CH_2)_3$— and $R_1R_2N(CH_2)_4$—, respectively.

The compounds of the present invention may be prepared by known organic synthesis techniques, including the methods described in more detail in the Examples. However in general, the compounds of structure (I) above may be made by the following Reaction Schemes. All substituents in the following Reaction Schemes are as defined above unless indicated otherwise.

For example, compounds of structure (II) may be synthesized according to Reaction Schemes A, B and C:

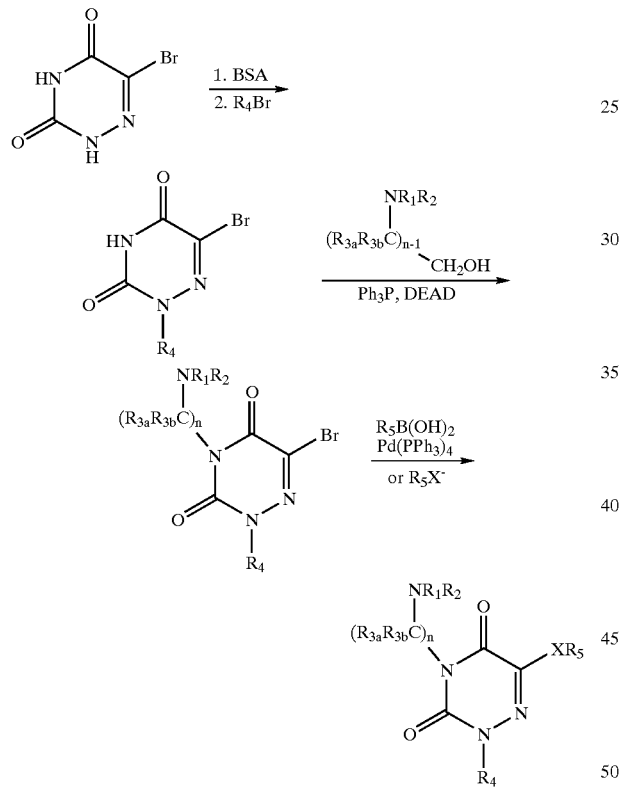

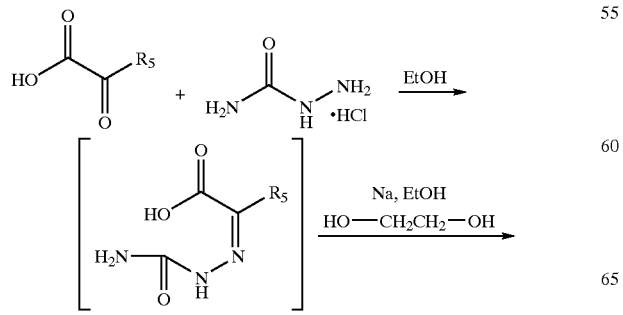

The 1,2,4-triazin-3,5-dione (isoazauracil) system may be synthesized as shown in the following Reaction Scheme D.

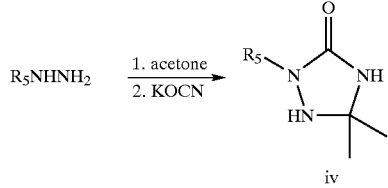

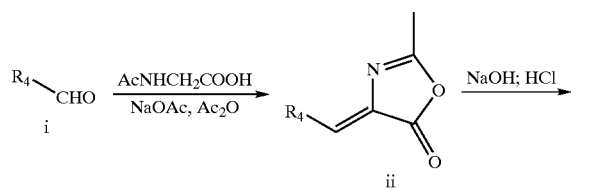

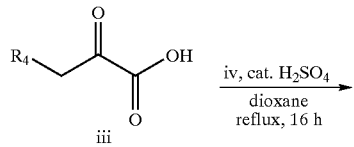

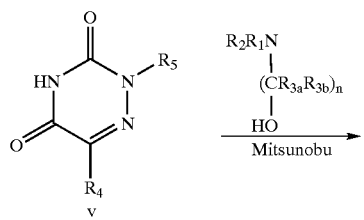

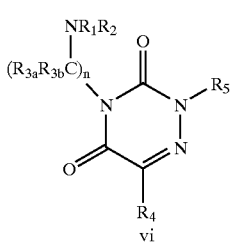

Triazolidinone iv may be prepared from phenylhydrazine. Pyruvic acid derivatives iii may be prepared from the corresponding azalactone ii, which in turn may be synthesized from aldehyde (Audia, et al. *J. Med Chem.* 1996, 39, 2773). Reaction of iii and iv under acid-catalyzed conditions results in the formation of isoazauracil v (see WO 86/00072). Coupling reactions of v with N-protected amino alcohols under Mitsunobu conditions yield the desired isoazauracils vi.

Compounds of structure (IV) may be prepared according to the following Reaction Scheme E.

Reaction Scheme E

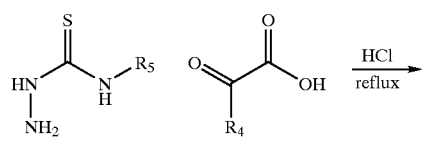

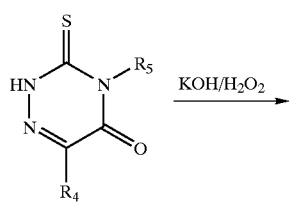

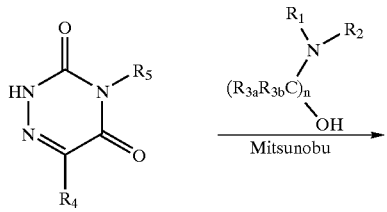

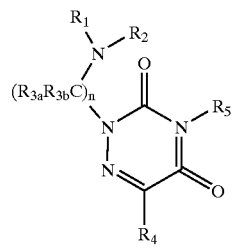

Compounds of structure (I) may generally be referred to as substituted 2H-[1,2,4]triazine-3,5-dione compounds, representative compounds of which include the following:

4-(2-Amino-2-phenyl-ethyl)-2-(2,6-difluoro-benzyl)-6-(2-fluoro-3-methoxy-phenyl)-2H-[1,2,4]triazine-3,5-dione;

4-(2-Amino-2-phenyl-ethyl)-2-(2,6-dichloro-benzyl)-6-(2-fluoro-3-methoxy-phenyl)-2H-[1,2,4]triazine-3,5-dione;

4-(2-Amino-2-phenyl-ethyl)-2-(2-fluoro-6-chloro-benzyl)-6-(2-fluoro-3-methoxy-phenyl)-2H-[1,2,4]triazine-3,5-dione;

4-(2-Amino-2-phenyl-ethyl)-2-(2-fluoro-6-trifluoromethyl-benzyl)-6-(2-fluoro-3-methoxy-phenyl)-2H-[1,2,4]triazine-3,5-dione;

4-(2-Amino-2-phenyl-ethyl)-2-(2-fluoro-6-methylsulfonyl-benzyl)-6-(2-fluoro-3-methoxy-phenyl)-2H-[1,2,4]triazine-3,5-dione;

4-(2 -Amino-2-phenyl-ethyl)-2-(2-fluoro-benzyl)-6-(2-fluoro-3-methoxy-phenyl)-2H-[1,2,4]triazine-3,5-dione;

4-(2-Amino-2-phenyl-ethyl)-2-(2-chloro-benzyl)-6-(2-fluoro-3-methoxy-phenyl)-2H-[1,2,4]triazine-3,5-dione;

4-(2-Amino-2-phenyl-ethyl)-2-(2-trifluoromethyl-benzyl)-6-(2-fluoro-3-methoxy-phenyl)-2H-[1,2,4]triazine-3,5-dione;

4-(2-Amino-2-phenyl-ethyl)-2-(2-methylsulfonyl-benzyl)-6-(2-fluoro-3-methoxy-phenyl)-2H-[1,2,4]triazine-3,5-dione;

4-(2-Amino-2-phenyl-ethyl)-2-(2,6-difluoro-benzyl)-6-(2-fluoro-phenyl)-2H-[1,2,4]triazine-3,5-dione;

4-(2-Amino-2-phenyl-ethyl)-2-(2,6-dichloro-benzyl)-6-(2-fluoro-phenyl)-2H-[1,2,4]triazine-3,5-dione;

4-(2-Amino-2-phenyl-ethyl)-2-(2-fluoro-6-chloro-benzyl)-6-(2-fluoro-phenyl)-2H-[1,2,4]triazine-3,5-dione;

4-(2-Amino-2-phenyl-ethyl)-2-(2-fluoro-6-trifluoromethyl-benzyl)-6-(2-fluoro-phenyl)-2H-[1,2,4]triazine-3,5-dione;

4-(2-Amino-2-phenyl-ethyl)-2-(2-fluoro-6-methylsulfonyl-benzyl)-6-(2-fluoro-phenyl)-2H-[1,2,4]triazine-3,5-dione;

4-(2-Amino-2-phenyl-ethyl)-2-(2-fluoro-benzyl)-6-(2-fluoro-phenyl)-2H-[1,2,4]triazine-3,5-dione;

4-(2-Amino-2-phenyl-ethyl)-2-(2-chloro-benzyl)-6-(2-fluoro-phenyl)-2H-[1,2,4]triazine-3,5-dione;

4-(2-Amino-2-phenyl-ethyl)-2-(2-trifluoromethyl-benzyl)-6-(2-fluoro-phenyl)-2H-[1,2,4]triazine-3,5-dione;

4-(2-Amino-2-phenyl-ethyl)-2-(2-methylsulfonyl-benzyl)-6-(2-fluoro-phenyl)-2H-[1,2,4]triazine-3,5-dione;

4-(2-Amino-2-phenyl-ethyl)-2-(2,6-difluoro-benzyl)-6-(2-chloro-phenyl)-2H-[1,2,4]triazine-3,5-dione;

4-(2-Amino-2-phenyl-ethyl)-2-(2,6-dichloro-benzyl)-6-(2-chloro-phenyl)-2H-[1,2,4]triazine-3,5-dione;
4-(2-Amino-2-phenyl-ethyl)-2-(2-fluoro-6-chloro-benzyl)-6-(2-chloro-phenyl)-2H-[1,2,4]triazine-3,5-dione;
4-(2-Amino-2-phenyl-ethyl)-2-(2-fluoro-6-trifluoromethyl-benzyl)-6-(2-chloro-phenyl)-2H-[1,2,4]triazine-3,5-dione;
4-(2-Amino-2-phenyl-ethyl)-2-(2-fluoro-6-methylsulfonyl-benzyl)-6-(2-chloro-phenyl)-2H-[1,2,4]triazine-3,5-dione;
4-(2-Amino-2-phenyl-ethyl)-2-(2-fluoro-benzyl)-6-(2-chloro-phenyl)-2H-[1,2,4]triazine-3,5-dione;
4-(2-Amino-2-phenyl-ethyl)-2-(2-chloro-benzyl)-6-(2-chloro-phenyl)-2H-[1,2,4]triazine-3,5-dione;
4-(2-Amino-2-phenyl-ethyl)-2-(2-trifluoromethyl-benzyl)-6-(2-chloro-phenyl)-2H-[1,2,4]triazine-3,5-dione;
4-(2-Amino-2-phenyl-ethyl)-2-(2-methylsulfonyl-benzyl)-6-(2-chloro-phenyl)-2H-[1,2,4]triazine-3,5-dione;
4-(2-Amino-2-phenyl-ethyl)-2-(2,6-difluoro-benzyl)-6-(3-methoxy-phenyl)-2H-[1,2,4]triazine-3,5-dione;
4-(2-Amino-2-phenyl-ethyl)-2-(2,6-dichloro-benzyl)-6-(3-methoxy-phenyl)-2H-[1,2,4]triazine-3,5-dione;
4-(2-Amino-2-phenyl-ethyl)-2-(2-fluoro-6-chloro-benzyl)-6-(3-methoxy-phenyl)-2H-[1,2,4]triazine-3,5-dione;
4-(2-Amino-2-phenyl-ethyl)-2-(2-fluoro-6-trifluoromethyl-benzyl)-6-(3-methoxy-phenyl)-2H-[1,2,4]triazine-3,5-dione;
4-(2-Amino-2-phenyl-ethyl)-2-(2-fluoro-6-methylsulfonyl-benzyl)-6-(3-methoxy-phenyl)-2H-[1,2,4]triazine-3,5-dione;
4-(2-Amino-2-phenyl-ethyl)-2-(2-fluoro-benzyl)-6-(3-methoxy-phenyl)-2H-[1,2,4]triazine-3,5-dione;
4-(2-Amino-2-phenyl-ethyl)-2-(2-chloro-benzyl)-6-(3-methoxy-phenyl)-2H-[1,2,4]triazine-3,5-dione;
4-(2-Amino-2-phenyl-ethyl)-2-(2-trifluoromethyl-benzyl)-6-(3-methoxy-phenyl)-2H-[1,2,4]triazine-3,5-dione;
4-(2-Amino-2-phenyl-ethyl)-2-(2-methylsulfonyl-benzyl)-6-(3-methoxy-phenyl)-2H-[1,2,4]triazine-3,5-dione;
4-(2-Amino-2-phenyl-ethyl)-2-(2,6-difluoro-benzyl)-6-(2-chloro-3-methoxy-phenyl)-2H-[1,2,4]triazine-3,5-dione;
4-(2-Amino-2-phenyl-ethyl)-2-(2,6-dichloro-benzyl)-6-(2-chloro-3-methoxy-phenyl)-2H-[1,2,4]triazine-3,5-dione;
4-(2-Amino-2-phenyl-ethyl)-2-(2-fluoro-6-chloro-benzyl)-6-(2-chloro-3-methoxy-phenyl)-2H-[1,2,4]triazine-3,5-dione;
4-(2-Amino-2-phenyl-ethyl)-2-(2-fluoro-6-trifluoromethyl-benzyl)-6-(2-chloro-3-methoxy-phenyl)-2H-[1,2,4]triazine-3,5-dione;
4-(2-Amino-2-phenyl-ethyl)-2-(2-fluoro-6-methylsulfonyl-benzyl)-6-(2-chloro-3-methoxy-phenyl)-2H-[1,2,4]triazine-3,5-dione;
4-(2-Amino-2-phenyl-ethyl)-2-(2-fluoro-benzyl)-6-(2-chloro-3-methoxy-phenyl)-2H-[1,2,4]triazine-3,5-dione;
4-(2-Amino-2-phenyl-ethyl)-2-(2-chloro-benzyl)-6-(2-chloro-3-methoxy-phenyl)-2H-[1,2,4]triazine-3,5-dione;
4-(2-Amino-2-phenyl-ethyl)-2-(2-trifluoromethyl-benzyl)-6-(2-chloro-3-methoxy-phenyl)-2H-[1,2,4]triazine-3,5-dione;
4-(2-Amino-2-phenyl-ethyl)-2-(2-methylsulfonyl-benzyl)-6-(2-chloro-3-methoxy-phenyl)-2H-[1,2,4]triazine-3,5-dione;
4-(2-Amino-2-phenyl-ethyl)-6-(2,6-difluoro-benzyl)-2-(2-fluoro-3-methoxy-phenyl)-2H-[1,2,4]triazine-3,5-dione;
4-(2-Amino-2-phenyl-ethyl)-6-(2,6-difluoro-benzyl)-2-(2-fluoro-3-methoxy-phenyl)-2H-[1,2,4]triazine-3,5-dione;
4-(2-Amino-2-phenyl-ethyl)-6-(2,6-dichloro-benzyl)-2-(2-fluoro-3-methoxy-phenyl)-2H-[1,2,4]triazine-3,5-dione;
4-(2-Amino-2-phenyl-ethyl)-6-(2-fluoro-6-chloro-benzyl)-2-(2-fluoro-3-methoxy-phenyl)-2H-[1,2,4]triazine-3,5-dione;
4-(2-Amino-2-phenyl-ethyl)-6-(2-fluoro-6-trifluoromethyl-benzyl)-2-(2-fluoro-3-methoxy-phenyl)-2H-[1,2,4]triazine-3,5-dione;
4-(2-Amino-2-phenyl-ethyl)-6-(2-fluoro-6-methylsulfonyl-benzyl)-2-(2-fluoro-3-methoxy-phenyl)-2H-[1,2,4]triazine-3,5-dione;
4-(2-Amino-2-phenyl-ethyl)-6-(2-fluoro-benzyl)-2-(2-fluoro-3-methoxy-phenyl)-2H-[1,2,4]triazine-3,5-dione;
4-(2-Amino-2-phenyl-ethyl)-6-(2-chloro-benzyl)-2-(2-fluoro-3-methoxy-phenyl)-2H-[1,2,4]triazine-3,5-dione;
4-(2-Amino-2-phenyl-ethyl)-6-(2-trifluoromethyl-benzyl)-2-(2-fluoro-3-methoxy-phenyl)-2H-[1,2,4]triazine-3,5-dione;
4-(2-Amino-2-phenyl-ethyl)-6-(2-methylsulfonyl-benzyl)-2-(2-fluoro-3-methoxy-phenyl)-2H-[1,2,4]triazine-3,5-dione;
4-(2-Amino-2-phenyl-ethyl)-6-(2,6-difluoro-benzyl)-2-(2-fluoro-phenyl)-2H-[1,2,4]triazine-3,5-dione;
4-(2-Amino-2-phenyl-ethyl)-6-(2,6-dichloro-benzyl)-2-(2-fluoro-phenyl)-2H-[1,2,4]triazine-3,5-dione;
4-(2-Amino-2-phenyl-ethyl)-6-(2-fluoro-6-chloro-benzyl)-2-(2-fluoro-phenyl)-2H-[1,2,4]triazine-3,5-dione;
4-(2-Amino-2-phenyl-ethyl)-6-(2-fluoro-6-trifluoromethyl-benzyl)-2-(2-fluoro-phenyl)-2H-[1,2,4]triazine-3,5-dione;
4-(2-Amino-2-phenyl-ethyl)-6-(2-fluoro-6-methylsulfonyl-benzyl)-2-(2-fluoro-phenyl)-2H-[1,2,4]triazine-3,5-dione;
4-(2-Amino-2-phenyl-ethyl)-6-(2-fluoro-benzyl)-2-(2-fluoro-phenyl)-2H-[1,2,4]triazine-3,5-dione;
4-(2-Amino-2-phenyl-ethyl)-6-(2-chloro-benzyl)-2-(2-fluoro-phenyl)-2H-[1,2,4]triazine-3,5-dione;
4-(2-Amino-2-phenyl-ethyl)-6-(2-trifluoromethyl-benzyl)-2-(2-fluoro-phenyl)-2H-[1,2,4]triazine-3,5-dione;
4-(2-Amino-2-phenyl-ethyl)-6-(2-methylsulfonyl-benzyl)-2-(2-fluoro-phenyl)-2H-[1,2,4]triazine-3,5-dione;
4-(2-Amino-2-phenyl-ethyl)-6-(2,6-difluoro-benzyl)-2-(2-chloro-phenyl)-2H-[1,2,4]triazine-3,5-dione;
4-(2-Amino-2-phenyl-ethyl)-6-(2,6-dichloro-benzyl)-2-(2-chloro-phenyl)-2H-[1,2,4]triazine-3,5-dione;
4-(2-Amino-2-phenyl-ethyl)-6-(2-fluoro-6-chloro-benzyl)-2-(2-chloro-phenyl)-2H-[1,2,4]triazine-3,5-dione;
4-(2-Amino-2-phenyl-ethyl)-6-(2-fluoro-6-trifluoromethyl-benzyl)-2-(2-chloro-phenyl)-2H-[1,2,4]triazine-3,5-dione;
4-(2-Amino-2-phenyl-ethyl)-6-(2-fluoro-6-methylsulfonyl-benzyl)-2-(2-chloro-phenyl)-2H-[1,2,4]triazine-3,5-dione;
4-(2-Amino-2-phenyl-ethyl)-6-(2-fluoro-benzyl)-2-(2-chloro-phenyl)-2H-[1,2,4]triazine-3,5-dione;
4-(2-Amino-2-phenyl-ethyl)-6-(2-chloro-benzyl)-2-(2-chloro-phenyl)-2H-[1,2,4]triazine-3,5-dione;
4-(2-Amino-2-phenyl-ethyl)-6-(2-trifluoromethyl-benzyl)-2-(2-chloro-phenyl)-2H-[1,2,4]triazine-3,5-dione;
4-(2-Amino-2-phenyl-ethyl)-6-(2-methylsulfonyl-benzyl)-2-(2-chloro-phenyl)-2H-[1,2,4]triazine-3,5-dione;
4-(2-Amino-2-phenyl-ethyl)-6-(2,6-difluoro-benzyl)-2-(3-methoxy-phenyl)-2H-[1,2,4]triazine-3,5-dione;
4-(2-Amino-2-phenyl-ethyl)-6-(2,6-dichloro-benzyl)-2-(3-methoxy-phenyl)-2H-[1,2,4]triazine-3,5-dione;
4-(2-Amino-2-phenyl-ethyl)-6-(2-fluoro-6-chloro-benzyl)-2-(3-methoxy-phenyl)-2H-[1,2,4]triazine-3,5-dione;
4-(2-Amino-2-phenyl-ethyl)-6-(2-fluoro-6-trifluoromethyl-benzyl)-2-(3-methoxy-phenyl)-2H-[1,2,4]triazine-3,5-dione;

4-(2-Amino-2-phenyl-ethyl)-6-(2-fluoro-6-methylsulfonyl-benzyl)-2-(3-methoxy-phenyl)-2H-[1,2,4]triazine-3,5-dione;

4-(2-Amino-2-phenyl-ethyl)-6-(2-fluoro-benzyl)-2-(3-methoxy-phenyl)-2H-[1,2,4]triazine-3,5-dione;

4-(2-Amino-2-phenyl-ethyl)-6-(2-chloro-benzyl)-2-(3-methoxy-phenyl)-2H-[1,2,4]triazine-3,5-dione;

4-(2-Amino-2-phenyl-ethyl)-6-(2-trifluoromethyl-benzyl)-2-(3-methoxy-phenyl)-2H-[1,2,4]triazine-3,5-dione;

4-(2-Amino-2-phenyl-ethyl)-6-(2-methylsulfonyl-benzyl)-2-(3-methoxy-phenyl)-2H-[1,2,4]triazine-3,5-dione;

4-(2-Amino-2-phenyl-ethyl)-6-(2,6-difluoro-benzyl)-2-(2-chloro-3-methoxy-phenyl)-2H-[1,2,4]triazine-3,5-dione;

4-(2-Amino-2-phenyl-ethyl)-6-(2,6-dichloro-benzyl)-2-(2-chloro-3-methoxy-phenyl)-2H-[1,2,4]triazine-3,5-dione;

4-(2-Amino-2-phenyl-ethyl)-6-(2-fluoro-6-chloro-benzyl)-2-(2-chloro-3-methoxy-phenyl)-2H-[1,2,4]triazine-3,5-dione;

4-(2-Amino-2-phenyl-ethyl)-6-(2-fluoro-6-trifluoromethyl-benzyl)-2-(2-chloro-3-methoxy-phenyl)-2H-[1,2,4]triazine-3,5-dione;

4-(2-Amino-2-phenyl-ethyl)-6-(2-fluoro-6-methylsulfonyl-benzyl)-2-(2-chloro-3-methoxy-phenyl)-2H-[1,2,4]triazine-3,5-dione;

4-(2-Amino-2-phenyl-ethyl)-6-(2-fluoro-benzyl)-2-(2-chloro-3-methoxy-phenyl)-2H-[1,2,4]triazine-3,5-dione;

4-(2-Amino-2-phenyl-ethyl)-6-(2-chloro-benzyl)-2-(2-chloro-3-methoxy-phenyl)-2H-[1,2,4]triazine-3,5-dione;

4-(2-Amino-2-phenyl-ethyl)-6-(2-trifluoromethyl-benzyl)-2-(2-chloro-3-methoxy-phenyl)-2H-[1,2,4]triazine-3,5-dione;

4-(2-Amino-2-phenyl-ethyl)-6-(2-methylsulfonyl-benzyl)-2-(2-chloro-3-methoxy-phenyl)-2H-[1,2,4]triazine-3,5-dione;

2-(2-Amino-2-phenyl-ethyl)-6-(2,6-difluoro-benzyl)-4-(2-fluoro-3-methoxy-phenyl)-2H-[1,2,4]triazine-3,5-dione;

2-(2-Amino-2-phenyl-ethyl)-6-(2,6-dichloro-benzyl)-4-(2-fluoro-3-methoxy-phenyl)-2H-[1,2,4]triazine-3,5-dione;

2-(2-Amino-2-phenyl-ethyl)-6-(2-fluoro-6-chloro-benzyl)-4-(2-fluoro-3-methoxy-phenyl)-2H-[1,2,4]triazine-3,5-dione;

2-(2-Amino-2-phenyl-ethyl)-6-(2-fluoro-6-trifluoromethyl-benzyl)-4-(2-fluoro-3-methoxy-phenyl)-2H-[1,2,4]triazine-3,5-dione;

2-(2-Amino-2-phenyl-ethyl)-6-(2-fluoro-6-methylsulfonyl-benzyl)-4-(2-fluoro-3-methoxy-phenyl)-2H-[1,2,4]triazine-3,5-dione;

2-(2-Amino-2-phenyl-ethyl)-6-(2-fluoro-benzyl)-4-(2-fluoro-3-methoxy-phenyl)-2H-[1,2,4]triazine-3,5-dione;

2-(2-Amino-2-phenyl-ethyl)-6-(2-chloro-benzyl)-4-(2-fluoro-3-methoxy-phenyl)-2H-[1,2,4]triazine-3,5-dione;

2-(2-Amino-2-phenyl-ethyl)-6-(2-trifluoromethyl-benzyl)-4-(2-fluoro-3-methoxy-phenyl)-2H-[1,2,4]triazine-3,5-dione;

2-(2-Amino-2-phenyl-ethyl)-6-(2-methylsulfonyl-benzyl)-4-(2-fluoro-3-methoxy-phenyl)-2H-[1,2,4]triazine-3,5-dione;

2-(2-Amino-2-phenyl-ethyl)-6-(2,6-difluoro-benzyl)-4-(2-fluoro-phenyl)-2H-[1,2,4]triazine-3,5-dione;

2-(2-Amino-2-phenyl-ethyl)-6-(2,6-dichloro-benzyl)-4-(2-fluoro-phenyl)-2H-[1,2,4]triazine-3,5-dione;

2-(2-Amino-2-phenyl-ethyl)-6-(2-fluoro-6-chloro-benzyl)-4-(2-fluoro-phenyl)-2H-[1,2,4]triazine-3,5-dione;

2-(2-Amino-2-phenyl-ethyl)-6-(2-fluoro-6-trifluoromethyl-benzyl)-4-(2-fluoro-phenyl)-2H-[1,2,4]triazine-3,5-dione;

2-(2-Amino-2-phenyl-ethyl)-6-(2-fluoro-6-methylsulfonyl-benzyl)-4-(2-fluoro-phenyl)-2H-[1,2,4]triazine-3,5-dione;

2-(2-Amino-2-phenyl-ethyl)-6-(2-fluoro-benzyl)-4-(2-fluoro-phenyl)-2H-[1,2,4]triazine-3,5-dione;

2-(2-Amino-2-phenyl-ethyl)-6-(2-chloro-benzyl)-4-(2-fluoro-phenyl)-2H-[1,2,4]triazine-3,5-dione;

2-(2-Amino-2-phenyl-ethyl)-6-(2-trifluoromethyl-benzyl)-4-(2-fluoro-phenyl)-2H-[1,2,4]triazine-3,5-dione;

2-(2-Amino-2-phenyl-ethyl)-6-(2-methylsulfonyl-benzyl)-4-(2-fluoro-phenyl)-2H-[1,2,4]triazine-3,5-dione;

2-(2-Amino-2-phenyl-ethyl)-6-(2,6-difluoro-benzyl)-4-(2-chloro-phenyl)-2H-[1,2,4]triazine-3,5-dione;

2-(2-Amino-2-phenyl-ethyl)-6-(2,6-dichloro-benzyl)-4-(2-chloro-phenyl)-2H-[1,2,4]triazine-3,5-dione;

2-(2-Amino-2-phenyl-ethyl)-6-(2-fluoro-6-chloro-benzyl)-4-(2-chloro-phenyl)-2H-[1,2,4]triazine-3,5-dione;

2-(2-Amino-2-phenyl-ethyl)-6-(2-fluoro-6-trifluoromethyl-benzyl)-4-(2-chloro-phenyl)-2H-[1,2,4]triazine-3,5-dione;

2-(2-Amino-2-phenyl-ethyl)-6-(2-fluoro-6-methylsulfonyl-benzyl)-4-(2-chloro-phenyl)-2H-[1,2,4]triazine-3,5-dione;

2-(2-Amino-2-phenyl-ethyl)-6-(2-fluoro-benzyl)-4-(2-chloro-phenyl)-2H-[1,2,4]triazine-3,5-dione;

2-(2-Amino-2-phenyl-ethyl)-6-(2-chloro-benzyl)-4-(2-chloro-phenyl)-2H-[1,2,4]triazine-3,5-dione;

2-(2-Amino-2-phenyl-ethyl)-6-(2-trifluoromethyl-benzyl)-4-(2-chloro-phenyl)-2H-[1,2,4]triazine-3,5-dione;

2-(2-Amino-2-phenyl-ethyl)-6-(2-methylsulfonyl-benzyl)-4-(2-chloro-phenyl)-2H-[1,2,4]triazine-3,5-dione;

2-(2-Amino-2-phenyl-ethyl)-6-(2,6-difluoro-benzyl)-4-(3-methoxy-phenyl)-2H-[1,2,4]triazine-3,5-dione;

2-(2-Amino-2-phenyl-ethyl)-6-(2,6-dichloro-benzyl)-4-(3-methoxy-phenyl)-2H-[1,2,4]triazine-3,5-dione;

2-(2-Amino-2-phenyl-ethyl)-6-(2-fluoro-6-chloro-benzyl)-4-(3-methoxy-phenyl)-2H-[1,2,4]triazine-3,5-dione;

2-(2-Amino-2-phenyl-ethyl)-6-(2-fluoro-6-trifluoromethyl-benzyl)-4-(3-methoxy-phenyl)-2H-[1,2,4]triazine-3,5-dione;

2-(2-Amino-2-phenyl-ethyl)-6-(2-fluoro-6-methylsulfonyl-benzyl)-4-(3-methoxy-phenyl)-2H-[1,2,4]triazine-3,5-dione;

2-(2-Amino-2-phenyl-ethyl)-6-(2-fluoro-benzyl)-4-(3-methoxy-phenyl)-2H-[1,2,4]triazine-3,5-dione;

2-(2-Amino-2-phenyl-ethyl)-6-(2-chloro-benzyl)-4-(3-methoxy-phenyl)-2H-[1,2,4]triazine-3,5-dione;

2-(2-Amino-2-phenyl-ethyl)-6-(2-trifluoromethyl-benzyl)-4-(3-methoxy-phenyl)-2H-[1,2,4]triazine-3,5-dione;

2-(2-Amino-2-phenyl-ethyl)-6-(2-methylsulfonyl-benzyl)-4-(3-methoxy-phenyl)-2H-[1,2,4]triazine-3,5-dione;

2-(2-Amino-2-phenyl-ethyl)-6-(2,6-difluoro-benzyl)-4-(2-chloro-3-methoxy-phenyl)-2H-[1,2,4]triazine-3,5-dione;

2-(2-Amino-2-phenyl-ethyl)-6-(2,6-dichloro-benzyl)-4-(2-chloro-3-methoxy-phenyl)-2H-[1,2,4]triazine-3,5-dione;

2-(2-Amino-2-phenyl-ethyl)-6-(2-fluoro-6-chloro-benzyl)-4-(2-chloro-3-methoxy-phenyl)-2H-[1,2,4]triazine-3,5-dione;

2-(2-Amino-2-phenyl-ethyl)-6-(2-fluoro-6-trifluoromethyl-benzyl)-4-(2-chloro-3-methoxy-phenyl)-2H-[1,2,4]triazine-3,5-dione;

2-(2-Amino-2-phenyl-ethyl)-6-(2-fluoro-6-methylsulfonyl-benzyl)-4-(2-chloro-3-methoxy-phenyl)-2H-[1,2,4]triazine-3,5-dione;

2-(2-Amino-2-phenyl-ethyl)-6-(2-fluoro-benzyl)-4-(2-chloro-3-methoxy-phenyl)-2H-[1,2,4]triazine-3,5-dione;

2-(2-Amino-2-phenyl-ethyl)-6-(2-chloro-benzyl)-4-(2-chloro-3-methoxy-phenyl)-2H-[1,2,4]triazine-3,5-dione;

2-(2-Amino-2-phenyl-ethyl)-6-(2-trifluoromethyl-benzyl)-4-(2-chloro-3-methoxy-phenyl)-2H-[1,2,4]triazine-3,5-dione; and 2-(2-Amino-2-phenyl-ethyl)-6-(2-methylsulfonyl-benzyl)-4-(2-chloro-3-methoxy-phenyl)-2H-[1,2,4]triazine-3,5-dione.

In addition, representative compounds of the present invention also include those compounds where the primary amine of the above named compounds is substituted with a substituted alkyl group or a cycloalkyl group. As described in the examples, one method of alkylating amines and amides is by reductive alkylation. There are many alternative methods well known in the chemical arts for accomplishing the reductive alkylation procedure, and there are many alternative alkylation methods. When an aldehyde, ketone, carboxylic acid, or acid chloride is treated with a primary or secondary amine in the presence of a reducing agent reductive alkylation may take place. Suitable reducing agents include (but are not limited to) sodium borohydride, sodium triacetoxyborohydride, sodium cyanoborohydride, hydrogen gas and a hydrogenation catalyst, zinc and hydrochloric acid, iron pentacarbonyl and alcoholic potassium hydroxide, formic acid, pyridine borohydride. Amines and amides may also be alkylated by the reaction of formaldehyde and a Mannich base or by the nucleophilic displacement of an alkyl halide or other leaving groups. As an example, the Mitsunobu reaction allows the alkylation of amines with primary or secondary alcohols and carboxylic acids by activation of the hydroxyl group with triphenylphosphine to form the leaving group triphenylphoshine oxide. Other commonly used alkylation methods are described in March, Advanced Organic Chemistry, 4th Ed., pp 1276–1277 (1992).

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I).

Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. Compounds of structure (I) may also possess axial chirality, which may result in atropisomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GnRH antagonists of this invention are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Spraque-Dawley rats are administered an GnRH antagonist in saline or other suitable formulation by oral gavage, sub-cutaneous injection, or intravenous injection. This is followed by sub-cutaneous injection of 200 ng GnRH in 0.2 mL saline. Thirty minutes after the last injection, the animals are decapitated and trunk blood collected. After centrifugation, the separated plasma is stored at −20° C. until determination of the LH and FSH by radioimmunoassay. Other techniques for determining the activity of GnRH receptor antagonists are well known in the field, such as the use of cultured pituitary cells for measuring GnRH activity (Vale et al., *Endocrinology* 91:562–572, 1972), and a technique for measuring radioligand binding to rat pituitary membranes (Perrin et al., *Mol. Pharmacol.* 23:44–51, 1983).

For example, effectiveness of a compound as a GnRH receptor antagonist may be determined by one or more of the following assays.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuraminidase for 9 min at 37° C. The digested tissue is then washed with 0.1% BSA/McCoy's 5A medium, and the washed cells suspended in 3% FBS/0.1 BSA/McCoy's 5A medium and plated into 96-well tissue culture plates at a cell density of 40,000 cells per well in 200 μl medium. The cells are then incubated at 37° C. for 3 days. One pituitary gland normally yields one 96-well plate of cells, which can be used for assaying three compounds. For assay of an GnRH antagonist, the incubated cells are first washed with 0.1% BSA/McCoy's 5A medium once, followed by addition of the test sample plus 1 nM GnRH in 200 μl 0.1% BSA/McCoy's 5A medium in triplicate wells. Each sample is assayed at 5-dose levels to generate a dose-response curve for determination of its potency on the inhibition of GnRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01 M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 μL of sample medium diluted 1:5 or rLH standard in RIA buffer and 100 μL of [125I]-labeled rLH (~30,000 cpm) plus 100 μL of rabbit anti-rLH antibody diluted 1:187,500 and 100 μL RIA buffer. The mixture is incubated at room temperature over-night. In the next day, 100 μL of goat anti-rabbit IgG diluted 1:20 and 100 μL of normal rabbit serum diluted 1:1000 are added and the mixture incubated for another 3 hours at room temperature. The incubated tubes are then centrifuged at 3,000 rpm for 30 minutes and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-Iodination of GnRH Peptide

The GnRH analog is labeled by the chloramine-T method. To 10 μg of peptide in 20 μL of 0.5M sodium phosphate buffer, pH 7.6, is added 1 mCi of Na125I, followed by 22.5 μg chloramine-T and the mixture vortexed for 20 sec. The reaction is stopped by the addition of 60 μg sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/ 0.1% TFA at −80° C. and can be used for up to 4 weeks.

GnRH Receptor Membrane Bindinz Assay

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 minutes.), and the supernatant centrifuged (20,000×g for 30 minutes, 4° C.) to collect the membrane fraction. The final membrane preparation is resuspended in binding buffer (10 mM Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GnRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 100 μM or less. In a preferred embodiment of this invention, the GnRH receptor antagonists have a $K_i$ of less than 10 μM, and more preferably less than 1 μM, and even more preferably less than 0.1 μM (i.e., 100 nM).

As mentioned above, the GnRH receptor antagonists of this invention have utility over a wide range of therapeutic applications, and may be used to treat a variety of sex-hormone related conditions in both men and women, as well as mammals in general. For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an angiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The following example is provided for purposes of illustration, not limitation. In summary, the GnRH receptor antagonists of this invention may be assayed by the general methods disclosed above, while the following Examples disclose the synthesis of representative compounds of this invention.

EXAMPLE 1

SYNTHESIS OF 4-[(2R)-AMINO-2-PHENETHYL]-2-(2,6-DIFLUOROBENZYL)-6-PHENYL-1,2,4-TRIAZINE-3,5-DIONE

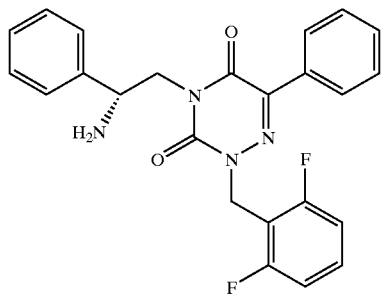

Step 1A 6-Phenyl-1,2,4-triazine-3,5-(2H,4H)-dione

To benzoylformic acid (10.0 g, 66.6 mmol) in water (30 mL) was added semicarbazide hydrochloride (6.66 g, 5.97 mmol) in water/ethanol (7:2, 180 mL). A thick white precipitate immediately formed, and vigorous stirring was continued for 16 hours. The mixture was filtered, and the precipitate was washed with water (2×5 mL), and dried in vacuo for 2 days to give the crude benzoylformic acid semicarbazone (12.2 g, 88%) as a white powder. [Dufresne, J. C.; Fleury, M. B. *Bull. Soc. Chim. Fr.* 1972, 2541.]

To absolute ethanol (50 mL) under nitrogen was added sodium (3.32 g, 144 mmol) in small chunks over 20 minutes. Upon complete consumption of the sodium, dry ethylene glycol (100 mL) and the benzoylformic acid semicarbazone (10.0 g, 48.2 mmol) were added, and the mixture was refluxed (120° C.) for 15 hours. The solvents were then distilled off in vacuo to leave a yellow solid. The residue was dissolved in water (60 mL) and acidified to pH 2 with concentrated HCl. The white precipate was collected by filtration, washed with water (2×10 mL), and dried in vacuo to give the desired compound as a tan powder (7.77 g, 85%). $^1$H NMR (DMSO-D$_6$, 360 MHz): 7.89–7.83 (m, 2H); 7.49–7.43 (m, 3H). [Daneshtalab, M.; Khalaj, A.; Lalezari, I. *J. Heterocycl. Chem.* 1979, 17, 817 and references sited therein.]

Step 1B 2-(2,6-Difluorobenzyl)-6-phenyl-1,2,4-triazine-3,5-(2H)-dione

To a stirring suspension of 6-phenyl-1,2,4-triazine-3,5-(2H,4H)-dione (6.00 g, 31.7 mmol) in dry acetonitrile (50 mL) under nitrogen was added bis(trimethylsilyl)acetamide (15.7 mL, 63.4 mmol). The resulting yellow solution was heated at 80° C. for 3 hours. The solution was cooled and 2,6-difluorobenzyl bromide (8.20 g, 39.6 mmol) was added in one portion. The mixture was heated at 80° C. under nitrogen for an additional 15 hours. The resulting solution was cooled to room temperature, quenched with methanol (20 mL), and diluted with dichloromethane (175 mL). The mixture was washed with water (75 mL) and brine (70 mL), and dried over magnesium sulfate. Evaporation gave a tan solid that was triturated with cold diethyl ether (5×5 mL). After drying in vacuo, the compound was isolated as a flocculent, off-white solid (8.80 g, 88%).

Step 1C 2-(2,6-Difluorobenzyl)-4-[(2R)-tert-butoxycarbonylamino-2-phenethyl]-6-phenyl-1,2,4-triazine-3,5-dione To a stirring suspension of 2-(2,6-difluorobenzyl)-6-phenyl-1,2,4-triazine-3,5-(2H)-dione (500 mg, 1.59 mmol), triphenylphosphine (625 g, 2.39 mmol) and N-BOC-D-phenylglycinol (425 g, 1.80 mmol) in dry THF (13 mL) was added diethyl azodicarboxylate (415 mg, 2.39 mmol) dropwise over 5 minutes. The mixture was stirred for 11 hours and concentrated to give a yellow solid. The solid was subjected to flash chromatography on silica gel (25% ethyl acetate:hexane) to give the protected compound as a flocculent off-white solid (488 mg, 58%).

Step 1D 2-(2,6-Difluorobenzyl)-4-[(2R)-amino-2-phenethyl]-6-phenyl-1,2,4-triazine-3,5-dione To 2-(2,6-difluorobenzyl)-4-[(2R)-tert-butoxycarbonylamino-2-phenethyl]-6-phenyl-1,2,4-triazine-3,5-dione (250 mg, 0.468 mmol) in dichloromethane (10 mL) was added trifluoroacetic acid (1 mL). The mixture was stirred for 1.5 hours and carefully quenched with saturated aqueous sodium bicarbonate (20 mL). The layers were separated, and the aqueous layer was extracted with dichloromethane (3×20 mL). The combined organics were dried over magnesium sulfate and evaporated to give the title compound as white platelets (200 mg, 99%). MS=435 (MH$^+$).

EXAMPLE 2

SYNTHESIS OF 4-[(2R)-AMINO-2-PHENETHYL]-2-(2,6-DIFLUOROBENZYL)-6-(2-FLUORO-3-METHOXYPHENYL)-1,2,4-TRIAZINE-3,5-DIONE

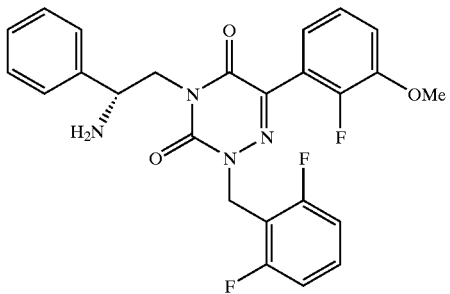

Step 2A 6-Bromo-2-(2,6-difluorobenzyl)-1,2,4-triazine-3,5-(2H)-dione

To a stirring suspension of 6-bromo- 1,2,4-triazine-3,5-(2H,4H)-dione [Dudfield, P. J.; Le, V-D.; Lindell, S. D.; Rees, C. W. *J. Chem. Soc. Perkin Trans* 1, 1999, 2929–2936] (2.78 g, 14.5 mmol) in dry acetonitrile (25 mL) under nitrogen was added bis(trimethylsilyl)acetamide (7.20 mL, 29.0 mmol). The resulting yellow solution was heated at 80° C. for 3 hours. The solution was cooled and 2,6-difluorobenzyl bromide (3.75 g, 18.1 mmol) was added in one portion. The mixture was heated at 80° C. under nitrogen for an additional 15 hours. The resulting solution was cooled to room temperature, quenced with methanol (10 mL), and diluted with dichloromethane (100 mL). The mixture was washed with water (40 mL) and brine (40 mL), and dried over magnesium sulfate. Evaporation gave a brown solid that was triturated with cold diethyl ether (5×5 mL). After drying in vacuo, the alkylated triazine was isolated as a pale orange solid (3.39 g, 74%). $^1$H NMR (DMSO-D$_6$, 360 MHz): 7.52–7.42 (m, 1H); 7.17–7.11 (m, 2H); 5.09 (s, 2H).

Step 2B 6-Bromo-4-[(2R)-tert-butoxycarbonylamino-2-phenethyl]-2-(2,6-difluorobenzyl)-1,2,4-triazine-3,5-dione To a stirring suspension of 6-bromo-2-(2,6-difluorobenzyl)-1,2,4-triazine-3,5-(2H)-dione (2.50 g, 7.86 mmol), triphenylphosphine (3.10 g, 11.8 mmol) and N-BOC-D-phenylglycinol (2.10 g, 8.85 mmol) in dry THF (70 mL) was added diethyl azodicarboxylate (2.06 g, 11.8 mmol) dropwise over 5 minutes. The mixture was stirred for 11 hours and concentrated to give a brown oil. The crude was subjected to flash chromatography on silica gel (30% ethyl acetate:hexane) to give compound as a flocculent off-white solid (3.77 g, 89%). $^1$H NMR (TMS/CDCl$_3$, 400 MHz): 7.39–7.28 (m, 6H); 6.97–6.90 (m, 2H); 5.33 (d, J=14.4 Hz, 1H); 5.25 (d, J=14.4 Hz, 1H); 5.17 (s, 2H); 4.44–4.34 (m, 1H); 4.06 (d, J=12.0 Hz, 1H); 1.35 (s, 9H). $^{13}$C NMR (TMS/CDCl$_3$, 100 MHz): 163.0, 160.5, 155.5, 153.2, 148.3, 138.7, 130.7, 129.0, 128.2, 126.4, 111.7, 111.4, 79.8, 52.8, 47.3, 44.0, 28.2. MS=438 (MH$^+$-Boc).

Step 2C 4-[(2R)-tert-Butoxycarbonylamino-2-phenethyl]-2-(2,6-difluorobenzyl)-6-(2-fluoro-3-methoxyphenyl)-1,2,4-triazine-3,5-dione A pressure tube fitted with a Teflon screw cap was charged with 6-bromo-4-[(2R)-tert-butoxycarbonylamino-2-phenethyl]-2-(2,6-difluorobenzyl)-1,2,4-triazine-3,5-dione (300 mg, 0.558 mmol), 2-fluoro-3-methoxyphenylboronic acid (142 mg, 0.837 mmol), DME:benzene:ethanol (10:9:1, 13.5 mL) and saturated aqueous barium hydroxide solution (4.8 mL). The mixture was degassed with nitrogen for 15 minutes and tetrakis(triphenylphosphine)palladium(0) (65 mg, 0.056 mmol) was added. The mixture was stirred rapidly and heated at 90° C. for 5 hours. The mixture was diluted with water (25 mL) and extracted with ethyl acetate (2×20 mL). The combined organics were washed with brine (30 mL), dried over magnesium sulfate, evaporated, and subjected to flash chromatography on silica gel (30% ethyl acetate:hexane) to give a pale yellow, viscous liquid (169 mg, 52%).

Step 2D 4-[(2R)-Amino-2-phenethyl]-2-(2,6-difluorobenzyl)-6-(2-fluoro-3-methoxyphenyl)-1,2,4-triazine-3,5-dione To 4-[(2R)-tert-butoxycarbonylamino-2-phenethyl]-2-(2,6-difluorobenzyl)-6-(2-fluoro-3-methoxyphenyl)-1,2,4-triazine-3,5-dione. (165 mg, 0.283 mmol) in dichloromethane (6 mL) was added trifluoroacetic acid (0.6 mL). The mixture was stirred for 1 hour and carefully quenched with saturated aqueous sodium bicarbonate (12 mL). The layers were separated, and the aqueous layer was extracted with dichloromethane (3×10 mL). The combined organics were dried over magnesium sulfate, evaporated, and subjected to flash chromatography on silica gel (5% methanol:dichloromethane) to give a glassy, pale yellow solid (169 mg, 77%). $^1$H NMR (TMS/CDCl$_3$, 400 MHz): 7.42–7.22 (m, 6H); 7.14–7.00 (m, 2H); 6.98–6.87 (m, 3H); 5.33 (s, 2H); 4.41 (dd, J=4.8, 9.6 Hz, 1H); 4.26 (dd, J=9.6, 12.8 Hz, 1H), 4.10 (dd, J=5.2, 13.2 Hz, 1H); 3.90 (s, 3H); 1.60 (s, 2H). $^{13}$C NMR (TMS/CDCl$_3$, 100 MHz): 163.0, 160.6, 155.1, 151.9, 149.3, 148.8, 143.5, 139.4, 130.5, 128.7, 127.6, 126.2, 123.8, 122.1, 115.0, 111.6, 111.4, 56.5, 54.0, 48.2, 44.1. MS=483 ((M+H)$^+$).

The representative compounds listed in table 1 were prepared according to the procedures set forth in this Example 2.

TABLE 1

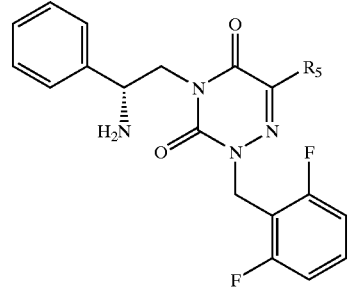

| Compound | R$_5$ | MW | MS (MH$^+$) |
|---|---|---|---|
| 2-2 | 2-Chlorophenyl | 486.8 | 469 |
| 2-3 | 2-Methylphenyl | 448.4 | 449 |
| 2-4 | 2-Ethylphenyl | 462.4 | 463 |
| 2-5 | 2-Methoxyphenyl | 464.4 | 465 |
| 2-6 | 2-Ethoxyphenyl | 478.4 | 479 |
| 2-7 | 2-Trifluoromethylphenyl | 502.4 | 503 |
| 2-8 | 2,3-Dimethylphenyl | 462.4 | 463 |
| 2-9 | 2,5-Dimethylphenyl | 462.4 | 463 |
| 2-10 | 2,4-Dichlorophenyl | 503.3 | 503 |
| 2-11 | 2-Fluoro-3-methoxyphenyl | 482.4 | 483 |
| 2-12 | 2,4-Dimethoxyphenyl | 494.4 | 495 |
| 2-13 | 2,5-Dimethoxyphenyl | 494.4 | 495 |
| 2-14 | 2-Methoxy-5-fluorophenyl | 482.4 | 483 |
| 2-15 | 2-Methoxy-5-methylphenyl | 478.4 | 479 |
| 2-16 | 2-Methoxy-5-isopropylphenyl | 506.5 | 507 |
| 2-17 | 2-Methoxy-5-chlorophenyl | 498.9 | 499 |
| 2-18 | 2,4,6-trimethylphenyl | 476.5 | 477 |
| 2-19 | 3-Benzothiophenyl | 490.5 | 491 |
| 2-20 | 8-Quinolinyl | 485.4 | 486 |
| 2-21 | 1-Naphthyl | 484.5 | 485 |

EXAMPLE 3

SYNTHESIS OF 4-[(2R)-AMINO-2-PHENETHYL]-2-(2,6-DIFLUOROBENZYL)-6-(2-FLUORO-3-METHOXYPHENYL)-1,2,4-TRIAZINE-3,5-DIONE

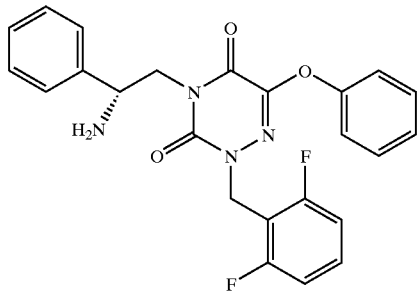

To 6-bromo-4-[(2R)-tert-butoxycarbonylamino-2-phenethyl]-2-(2,6-difluorobenzyl)-1,2,4-triazine-3,5-dione (100 mg, 0.186 mmol) in anhydrous ethanol (3 mL) was added pyridine (0.075 mL), and phenol (0.23 mmol). The mixture was refluxed for 15 hours, then concentrated. The residue was dissolved in dichloromethane (4 mL), and trifluoroacetic acid (0.4 mL) was added. The solution was stirred for 1 h, then concentrated and purified by preparative HPLC to give the title compound. $^1$H NMR (TMS/CDCl$_3$, 360 MHz): 7.42–7.15 (m, 9H); 7.03–6.98 (m, 2H); 6.86–6.79 (m, 2H); 6.98–6.87 (m, 2H); 5.33 (s, 2H); 4.42 (dd, J=5.8, 11.9 Hz, 1H); 4.33–4.23 (m, 1H); 4.10 (dd, J=5.8, 15.5 Hz, 1H); 1.59 (s, 2H).

The following representative compounds listed in Table 2 were synthesized according to the above procedure.

TABLE 2

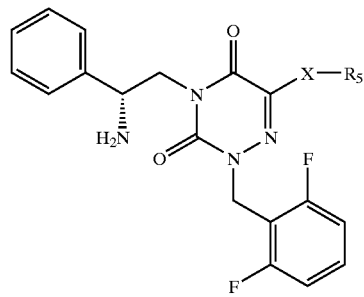

| Compound | —X—R$_5$ | MS (MH$^+$) |
|---|---|---|
| 3-1 | PhO | 451 |
| 3-2 | PhS | 467 |
| 3-3 | 2-FPhS | 485 |
| 3-4 | 1-Pyrrolidine | 428 |
| 3-5 | 1-Morpholine | 444 |

EXAMPLE 4

SYNTHESIS OF 6-(2,6-DIFLUOROBENZYL)-2-PHENYL-1,2,4-TRIAZINE-3,5-(4H)-DIONE

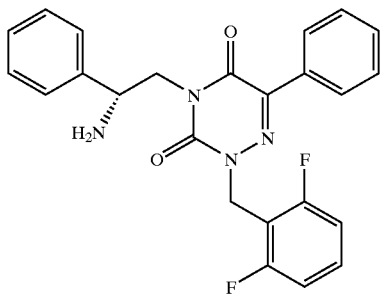

Step 4A. 6-(2,6-Difluorobenzyl)-2-phenyl-1,2,4-triazine-3,5-(4H)-dione.

To a mixture of the 2-phenyl-5,5-dimethyltriazolidinone (prepared according to a procedure described in US Patent WO86/00072.) (0.45 g, 2.4 mmol) and (2,6-difluorophenyl)pyruvic acid (prepared by the method of Audia, et al. *J. Med. Chem.* 1996, 39, 2773) (0.50 g, 2.5 mmol) in para-dioxane (8 mL) was added one drop of concentrated sulfuric acid. The mixture was stirred for 1.5 hoursunder ambient conditions. An additional 0.50 g of (2,6-difluorophenyl)pyruvic acid was added, then the mixture was refluxed for 4 hours. Two more drops of conc. H$_2$SO$_4$ were added, and the mixture was refluxed for an additional 18 hours. After cooling, the mixture was concentrated, diluted with water (10 mL) and extracted with ethyl acetate (3×10 mL). The combined organics were washed with brine (5 mL), dried over sodium sulfate, and concentrated. The crude was subjected to flash chromatography on silica gel (2% to 5% methanol:dichloromethane) to give an impure yellow oil (0.240 g, 32%).

Step 4B. 4-[(2R)-Amino-2-phenylethyl]- 6-(2,6-difluorobenzyl)-2-phenyl-1,2,4-triazine-3,5-dione.

To a stirring suspension of 6-(2,6-difluorobenzyl)-2-phenyl-1,2,4-triazine-3,5-(4H)-dione (0.100 g, 0.317 mmol), triphenylphosphine (0.13 g, 0.48 mmol) and N-BOC-D-phenylglycinol (0.083 g, 0.35 mmol) in dry THF (5 mL) was added diethyl azodicarboxylate (0.080 g, 0.48 mmol) dropwise over 5 minutes. The mixture was stirred for 11 h, then concentrated to give a yellow solid. The crude was subjected to flash chromatography on silica gel (20% ethyl acetate:hexane) to give a 117 mg of viscous, pale yellow oil. To the oil in dichloromethane (4 mL) was added trifluoroacetic acid (0.5 mL). The mixture was stirred for 30 minutes, evaporated to dryness, re-dissolved in 5 mL dichloromethane, and carefully quenched with saturated aqueous sodium bicarbonate (5 mL). The layers were separated, and the aqueous layer was extracted with dichloro-methane (2×5 mL). The combined organics were dried over magnesium sulfate, evaporated, and subjected to flash chromatography on silica gel (1% methanol:dichloromethane to 100% methanol) to give the title compound as a viscous yellow oil (0.060 g, 43%). $^1$H NMR (TMS/CDCl$_3$, 300 MHz): 7.45–7.11 (m, 11H); 6.93–6.81 (m, 2H); 4.43 (dd, J=4.0, 9.3 Hz, 1H); 4.31 (dd, J=9.9, 12.9 Hz, 1H), 4.10–4.05 (m, 1H); 4.10 (s, 2H); 1.92 (bs, 2H). MS (EI) m/e 435.1 (MH$^+$).

6-(2,6-Difluorobenzyl)-2-(2-fluorophenyl)-1,2,4-triazine-3,5-(4H)-dione was synthesized according to a procedure similar to example 4. MS (EI) m/e 453 (MH$^+$).

EXAMPLE 5

SYNTHESIS OF 2-[(2R)-AMINO-2-PHENETHYL]-4-PHENYL-6-(2,6-DIFLUOROBENZYL)-(1,2,4)-TRIAZIN-3,5-DIONE

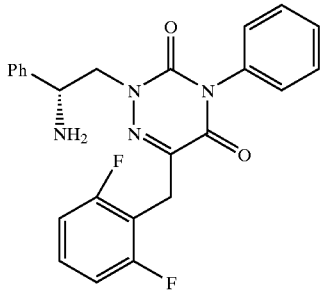

Step 5A. 4-Phenyl-6-(2,6-difluorobenzyl)-5-thioxo-2H-(1,2,4)triazin-3-one

Concentrated HCl (1.5 mL) was added to a solution of 2,6-difluorophenylpyruvic acid (1.0 g, 5.0 mmol) and 4-phenyl-3-thiosemicarbazide (836 mg, 5.0 mmol) in water (25 mL). The reaction mixture was refluxed for 16 hr and cooled to ambient temperature. The precipitate was filtered and washed with water extensively to give a white solid (1.54 g, 93.2%). MS (CI) m/z 332.1 (MH$^+$).

Step 5B. 4-Phenyl-6-(2,6-difluorobenzyl)-2H-(1,2,4)triazin-3,5-dione

4-Phenyl-6-(2,6-difluorobenzyl)-5-thioxo-2H-(1,2,4)triazin-3-one (1.00 g, 3.02 mmol) was dissolved in a solution of KOH (643 mg) in MeOH (12 mL) and water (6 mL). A solution of H$_2$O$_2$ (1.2 mL, 30% in water) in water (5 mL) was added and the reaction mixture was stirred at ambient temperature for 30 minutes. The reaction mixture was acidified with conc. HCl (1.1 mL) and a white solid precipitated. Filtered and washed with water to give a white solid (816 mg, 85.8%): MS (CI) m/z 380.2 (MH$^+$).

Step 5C. 2-[(2R)-amino-2-phenethyl]-4-phenyl-6-(2,6-difluorobenzyl)-(1,2,4)-triazin-3,5-dione A solution of N-(t-butyloxycarbonyl)-D-α-phenylglycinol (24 mg, 0.1 mmol) in anhydrous THF (2 mL) was treated with 4-phenyl-6-(2,6-difluorobenzyl)-2H-(1,2,4)triazin-3,5-dione (32 mg, 0.1 mmol) and polymer-supported triphenylphosphine (120 mg, loading 1 mmol PPh$_3$/g) at ambient temperature, then di-tert-butylazodicarboxylate (34 mg, 0.15 mmol) was introduced. The reaction mixture was stirred at ambient temperature for 16 hours. Filtered and the solid material was washed with more THF, organic filtrates were combined and volatiles were evaporated. Dichloromethane (1 mL) was added to the residue, TFA (1 mL) was added and the reaction mixture was stirred at ambient temperature for 1 hour. Volatiles were evaporated and the residue purified by reverse phase HPLC (C-18 column, 15–75% ACN/water) to give the title compound. $^1$H NMR (CDCl$_3$) δ 3.92 (d, J=13.5 Hz, 1H), 4.01 (s, 2H), 4.34–4.38 (m, 1H), 4.50–4.57 (m, 1H), 6.97–7.38 (m, 13H); MS (CI) m/z 435.10 (MH$^+$).

2-[(2R)-Amino-2-phenethyl]-4-(3-methoxyphenyl)-6-(2,6-difluorobenzyl)-(1,2,4)-triazin-3,5-dione was synthesized according to a procedure similar to Example 1. $^1$H NMR (CDCl$_3$) δ 3.70 (s, 3H), 3.93 (d, J=13.8, 1H), 4.01 (s, 2H), 4.35 (d, J=9.6 Hz, 1H), 4.56 (dd, J=13.8, 9.6 Hz, 1H), 6.71–7.35 (m, 12H); MS (CI) m/z 465.10 (MH$^+$).

It will be appreciated that, although specific embodiments of the invention have been described herein for purposes of illustration, various modifications may be made without departing from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

---

We claim:
1. A compound having the following structure:

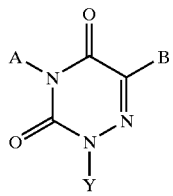

or a stereoisomer, or pharmaceutically acceptable salt thereof,
wherein:
A is —$(CR_{3a}R_{3b})_n NR_1R_2$ or $R_5$;
Y is —$(CR_{3a}R_{3b})_n NR_1R_2$, $R_4$, or $R_5$;
with the proviso that one of A or Y, but not both, is —$(CR_{3a}R_{3b})_n NR_1R_2$;
B is $R_4$ or —X—$R_5$;
X is a bond;
n is 2, 3 or 4;
$R_1$ and $R_2$ are the same or different and independently hydrogen, alkyl, substituted alkyl, aryl, substituted aryl, arylalkyl, substituted arylalkyl, heterocycle, substituted heterocycle, heterocyclealkyl, substituted heterocyclealkyl, —$C(R_8)(=NR_9)$ or —$C(NR_6R_7)(=NR_9)$;
or $R_1$ and $R_2$ taken together with the nitrogen atom to which they are attached form a heterocycle or a substituted heterocycle;
$R_{3a}$ and $R_{3b}$ are the same or different and, at each occurrence, independently hydrogen, alkyl, substituted alkyl, alkoxy, alkylthio, alkylamino, aryl, substituted aryl, arylalkyl, substituted arylalkyl, heterocycle, substituted heterocycle, heterocyclealkyl, substituted heterocyclealkyl, —$COOR_{10}$ or —$CONR_6R_7$;
or $R_{3a}$ and $R_{3b}$ taken together with the carbon atom to which they are attached form a homocycle, substituted homocycle, heterocycle or substituted heterocycle;
or $R_{3a}$ and the carbon to which it is attached taken together with $R_1$ and the nitrogen to which it is attached form a heterocycle or substituted heterocycle;
$R_4$ is arylalkyl, substituted arylalkyl, heteroarylalkyl or substituted heteroarylalkyl;
$R_5$ is aryl or substituted aryl;
$R_6$ and $R_7$ are the same or different independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_8$ is independently hydrogen, alkyl, substituted alkyl, aryl, substituted aryl, arylalkyl, substituted arylalkyl, heterocycle, substituted heterocycle, heterocyclealkyl or substituted heterocyclealkyl;

$R_9$ is independently hydrogen, alkyl, substituted alkyl, aryl, substituted aryl, arylalkyl, substituted arylalkyl, heterocycle, substituted heterocycle, heterocyclealkyl or substituted heterocyclealkyl; and $R_{10}$ is hydrogen, alkyl, or substituted alkyl.

2. The compound of claim 1 wherein A is —$(CR_{3a}R_{3b})_n NR_1R_2$.

3. The compound of claim 1 wherein Y is —$(CR_{3a}R_{3b})_n NR_1R_2$.

4. The compound of claim 1 wherein B is —X—$R_5$.

5. The compound of claim 1 wherein $R_1$ is hydrogen, alkyl, substituted alkyl, arylalkyl, substituted arylalkyl, heterocyclealkyl or substituted heterocyclealkyl.

6. The compound of claim 1 wherein $R_4$ is substituted arylalkyl.

7. The compound of claim 1 wherein $R_5$ is substituted aryl.

8. A pharmaceutical composition comprising a compound of claim 1 and a pharmaceutically acceptable carrier or diluent.

9. A method for treating benign prostatic hypertrophy or myoma of the uterus of a subject in need thereof, comprising administering to the subject an effective amount of the pharmaceutical composition of claim 8.

10. A method of treating a cancer in a subject in need thereof, comprising administering to the subject an effective amount of the pharmaceutical composition of claim 8, wherein the cancer is prostatic cancer, uterine cancer, breast cancer or pituitary gonadotroph adenomas.

11. A method for treating endometriosis, polycystic ovarian disease, uterine fibroids or precocious puberty of a subject in need thereof, comprising administering to the subject an effective amount of the pharmaceutical composition of claim 8.

12. A method for preventing pregnancy of a subject in need thereof, comprising administering an effective amount of the pharmaceutical composition of claim 8.

13. A method for treating lupus erythematosis, irritable bowel syndrome, premenstrual syndrome, hirsutism, short stature or sleep disorders of a subject in need thereof, comprising administering to the subject an effective amount of the pharmaceutical composition of claim 8.

* * * * *